United States Patent [19]

Merkel et al.

[11] Patent Number: 4,923,791

[45] Date of Patent: May 8, 1990

[54] PHOTOGRAPHIC RECORDING MATERIAL CONTAINING A CYAN DYE-FORMING COUPLER

[75] Inventors: Paul B. Merkel; David Hoke, both of Rochester, N.Y.

[73] Assignee: Eastman Kodak Company, Rochester, N.Y.

[21] Appl. No.: 335,167

[22] Filed: Apr. 7, 1989

[51] Int. Cl.$^5$ .............................................. G03C 1/08
[52] U.S. Cl. ..................................... 430/553; 430/552
[58] Field of Search ................................. 430/552, 553

[56] References Cited

U.S. PATENT DOCUMENTS 4,333,999  6/1982  Lau ........................................ 430/17
4,849,328  7/1989  Hoke et al. .......................... 430/553

OTHER PUBLICATIONS

Research Disclosure 17618 "Process for Forming Color Images" Dec. 1978, No. 176, pp. 53–56.

Primary Examiner—Paul R. Michl
Assistant Examiner—Janet C. Baxter
Attorney, Agent, or Firm—Richard E. Knapp

[57] ABSTRACT

A photographic recording material is disclosed which contains a phenolic cyan dye-forming coupler which has a carbonamido group or a ureido substituted group in the 2-position of the phenolic ring, and a ballast containing acylamino group in the 5-position of the ring. The ballast moiety comprises a sulfoxide, an amide, an ester, or a ketone group or a phosphine oxide group.

11 Claims, No Drawings

PHOTOGRAPHIC RECORDING MATERIAL CONTAINING A CYAN DYE-FORMING COUPLER

The present invention relates to a photographic material containing a phenolic cyan dye forming coupler. More particularly, this invention relates to couplers which are used to obtain a cyan dyes for color photography which are typically phenols and naphthols which yield azomethine dyes upon coupling with oxidized aromatic primary amino color developing agents.

The known couplers, including those of U.S. Pat. No. 4,333,999, have highly desirable properties in that they can provide dyes of excellent purity and hues which are shifted bathochromically to the long wavelength red absorption region. Although such couplers have been widely used, further improvements in coupler reactivity and enhanced dye absorption continue to be sought. For example, it has been difficult to obtain, with the same coupler, a dye having both high density and high coupling effectiveness. A cyan coupler yielding enhanced dye density yield allows use of less image coupler in a layer. This provides enhanced cost savings as well as image sharpness improvements. Coupling effectiveness is measured by comparing the gamma or contrast of the resulting dye image sensitometric test curve with that of a control coupler under identical conditions.

A highly desirable property of cyan dye forming couplers is their ability to provide acceptable dye densities while at the same time continuing to provide the levels of both deep wavelength absorption in the red region of the visible spectrum and hue purity in subsequently obtained cyan dyes.

The present invention provides a photographic recording material comprising a support and a photosensitive silver halide emulsion which has associated therewith a cyan dye forming coupler coupler compound having the structural formula:

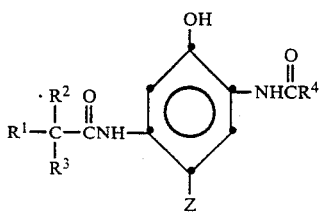

wherein:
R$^1$ is an unsubstituted or a substituted, straight or branched chain alkyl group having from 1 to about 20 carbon atoms, an unsubstituted or a substituted cycloalkyl group having from 3 to about 8 carbon atoms in the ring, or an unsubstituted or a substituted aryl group;
R$^2$ is as defined for R$^1$ or is hydrogen;
R$^3$ is a ballast group comprising one of the following:
(a) a sulfoxide containing group having the formula R$^5$—SO—;
(b) an amide containing group having the formula R$^6$R$^7$N—CO;
(c) an ester containing group having the formula R$^5$OCO;
(d) a ketone containing group having the formula

(e) a phosphine oxide containing group having the formula

R$^4$ represents an unsubstituted linear or branched aliphatic group or a linear or branched aliphatic group substituted with one or more substituents selected from a halogen atom, preferably chloro or fluoro, an alkoxy group an alkylthio group, an arylthio group, an alkylsulfonyl group, an arylsulfonyl group, a sulfonamido group, an acylamino group, an alkyloxycarbonyl group, an aryloxycarbonyl group, a carbamoyl group, an alkylcarbonyloxy group, an arylcarbonyloxy group, a carboxyl group and a hydroxyl group; or R$^4$ represents

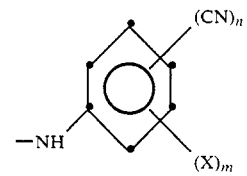

where X is —OCOR$^{10}$, —SO$_2$OR$^{10}$,

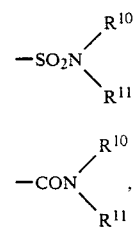

—NO$_2$, CF$_3$, hydrogen, halogen, hydroxy or a monovalent organic group;
R$^5$ is alkyl, cycloalkyl, aryl or heterocyclic which may be substituted;
R$^6$ and R$^7$, which may be the same or different, represent hydrogen or are as defined for R$^5$;
R$^8$ and R$^9$, which may be the same or different, represent alkyl, alkoxy, cycloalkyl, aryl or aryloxy which may be substituted;
R$^{10}$ is an alkyl group having up to 16 carbon atoms or an aryl group having from 6 to 12 carbon atoms;
R$^{11}$ is hydrogen, or as defined for R$^{10}$;
n is 0, 1 or 2;
m is 3 to 5; and
Z is hydrogen or a coupling off group; with the proviso that at least one of R$^1$, R$^2$, R$^3$ or Z is of such size and configuration as to render the coupler compound substantially nondiffusible in the layer of a photographic recording material in which it is coated.

The ballast moiety of the coupler compounds described in this invention differs from known couplers in that it has a sulfoxide, an amide, an ester, a ketone or a phosphine oxide group bonded to the carbon atom positioned alpha to the carbonyl group of the 5 substituted acylamino group. The acylamino group bonds the ballast moiety to the parent phenolic coupler moiety.

In preferred coupler compounds useful in this invention $R^2$ is hydrogen or alkyl of from 1 to about 4 carbon atoms. When the $R^1$ and $R^2$ groups are substituted, such substituents include hydroxy, halogen, or alkoxy having from 1 to about 8 carbon atoms.

Other preferred coupler compounds useful in this invention include those wherein $R^1$ is an alkyl group having from 1 to about 14 carbon atoms and $R^2$ is hydrogen.

Still further preferred coupler compounds are those wherein $R^4$ represents

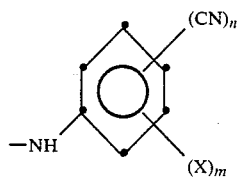

where X is $-COOR^{10}$, $-COR^{10}$, $-SO_2OR^{10}$,

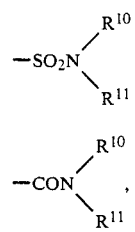

$-NO_2$, $-CF_3$, hydrogen, halogen, hydroxy or a monovalent organic group.

Especially preferred coupler compounds are those in the above formula wherein X is hydrogen, m is 4 and n is 1.

The monovalent organic group which can be represented by X can be alkyl, cycloalkyl or aryl groups having up to about 16 carbon atoms.

Preferably, $R^5$ is an unsubstituted or a substituted alkyl group having from 1 to about 24 carbon atoms, an unsubstituted or a substituted cycloalkyl group having from 3 to about 8 carbon atoms in the ring, an unsubstituted or a substituted aryl group having from 6 to about 24 carbon atoms, or an unsubstituted or a substituted heterocyclic group having from 3 to about 8 atoms in the heterocyclic ring, wherein the hetero ring atoms can be nitrogen, oxygen or sulfur.

$R^8$ and $R^9$, which may be the same or different, represent unsubstituted or substituted alkyl or alkoxy groups having from 1 to about 24 carbon atoms, unsubstituted or substituted cycloalkyl groups having from 3 to about 8 carbon atoms in the ring, or unsubstituted or substituted aryl or aryloxy groups having from 6 to about 24 carbon atoms.

When the $R^5$, $R^6$, $R^7$, $R^8$ or $R^9$ groups are substituted such substituents may include alkyl, aryl, alkoxy, aryloxy, alkylthio, arylthio, hydroxy, halogen, alkoxycarbamyl, aryloxycarbonyl, carboxy, acyl, acyloxy, carbonamido, carbamoyl, alkylsulfonyl, arylsulfonyl, sulfonamido and sulfamoyl groups wherein the alkyl and aryl substituents, and the alkyl and aryl moieties of the alkoxy, aryloxy, alkylthio, arylthio, alkoxycarbonyl, arylcarbonyl, acyl, acyloxy, carbonamido, carbamoyl, alkylsulfonyl, arylsulfonyl, sulfonamido and sulfamoyl substituents can contain, respectively, from 1 to about 30 carbon atoms and from 6 to about 30 carbon atoms and can be further substituted with such substituents.

Coupling off groups defined by Z are well known to those skilled in the art. Such groups can determine the equivalency of the coupler i.e., whether it is a 2-equivalent coupler or a 4-equivalent coupler. Such groups can also modify the reactivity of the coupler or can advantageously affect the layer in which the coupler is coated, or other layers in a photographic recording material, by performing, after release from the coupler, various photographic functions, such as development inhibition, bleach inhibition, bleach acceleration and color correction.

Representative classes of coupling off groups include alkoxy, aryloxy, heteroyloxy, sulfonyloxy, acyloxy, acyl, heterocyclyl, sulfonamido, phosphonyloxy and arylazo. These coupling off groups are described in the art, for example, in U.S. Pat. Nos. 2,455,169, 3,227,551, 3,432,521, 3,476,563, 3,617,291, 3,880,661, 4,052,212 and 4,134,766; and in U.K. patents and published applications Nos. 1,466,728, 1,531,927, 1,533,039, 2,006,755A and 2,017,704A, the disclosures of which are incorporated herein by reference.

Examples of preferred coupling off groups which can be represented by Z are:

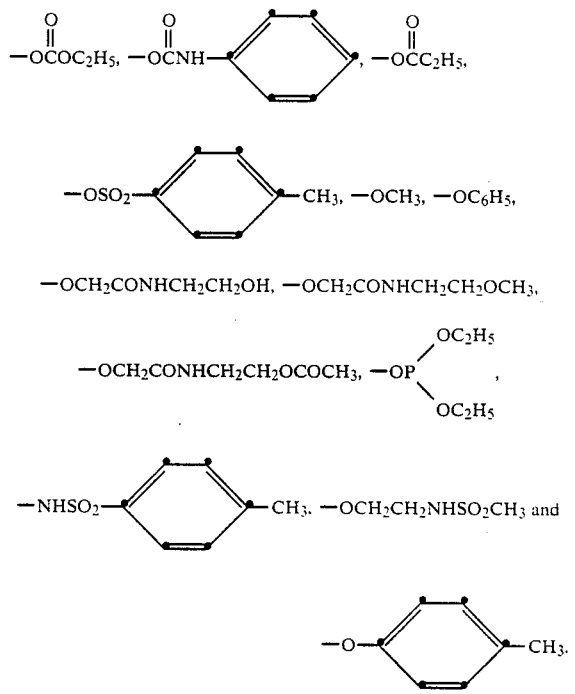

Especially preferred Z groups are hydrogen and

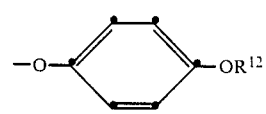

where $R^{12}$ is an alkyl group having from 1 to about 10 carbon atoms, such as

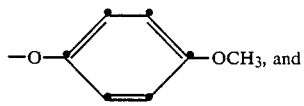—OCH₃, and

—OC₈H₁₇.

Specific coupler compounds of this invention are shown below in Table 1 with reference to the following structural formula:

TABLE 1

$$\begin{array}{c} \text{OH} \\ R^1-\underset{R^3}{\overset{R^2}{C}}-\overset{O}{\underset{}{C}}NH-\underset{Z}{\bigcirc}-NH\overset{O}{\underset{}{C}}R^4 \end{array}$$

| Coupler Compound | R¹ | R² | R³ | R⁴ | Z* |
|---|---|---|---|---|---|
| 1 | —C₂H₅ | H | —SOC₁₆H₃₃ | 3,4-dichlorophenyl | A |
| 2 | i-C₃H₇ | H | —SOC₁₆H₃₃ | 4-chlorophenyl | A |
| 3 | —C₁₀H₂₁ | H | —SOC₁₆H₃₃ | phenyl | H |
| 4 | —C₂H₅ | H | —COC₁₆H₃₃ | —C₃F₇ | B |
| 5 | -i-C₃H₇ | H | —COC₁₆H₃₃ | 3,4-dichlorophenyl | A |
| 6 | —C₁₀H₂₁ | H | —COC₁₆H₃₃ | 4-chlorophenyl | H |
| 7 | —C₂H₅ | H | —CON(C₈H₁₇)₂ | 4-chlorophenyl | A |
| 8 | -i-C₃H₇ | H | —CON(C₈H₁₇)₂ | 3,5-dichlorophenyl | B |
| 9 | —C₁₀H₂₁ | CH₃ | —CON(CH₃)₂ | 3,4-dichlorophenyl | H |

TABLE 1-continued

Structure: R¹-C(R²)(R³)-C(=O)-NH-[phenyl with OH top, NHC(=O)R⁴ right, Z bottom]

| Coupler Compound | R¹ | R² | R³ | R⁴ | Z* |
|---|---|---|---|---|---|
| 10 | —C₂H₅ | H | —COC₁₆H₃₃ (C=O) | C₃F₇ | A |
| 11 | -i-C₃H₇ | H | —COC₁₆H₃₃ (C=O) | phenyl-Cl | A |
| 12 | —C₁₀H₂₁ | CH₃ | —COC₁₆H₃₃ | phenyl-CN | H |
| 13 | —C₂H₅ | H | —P(=O)(C₂H₅)₂ | phenyl-Cl | A |
| 14 | —C₂H₅ | H | —P(=O)(CH₃)(C₁₆H₃₃) | phenyl-Cl,Cl | A |
| 15 | —C₂H₅ | H | —P(=O)(OC₆H₅)₂ | phenyl-Cl | H |

*A = —O-phenyl-OCH₃

B = —O-phenyl-OC₈H₁₇

Further specific coupler compounds useful in this invention are shown below in Table 2 with reference to the following structural formula:

TABLE 2

Structure: R¹-C(R²)(R³)-C(=O)-NH-[phenyl with OH, Z]-NH-C(=O)-NH-phenyl-CN

| Coupler Compound | R¹ | R² | R³ | Z* |
|---|---|---|---|---|
| 16 | —C₂H₅ | H | —SOC₁₆H₃₃ | A |
| 17 | i-C₃H₇ | H | —SOC₁₆H₃₃ | A |
| 18 | —C₁₀H₂₁ | H | —SOC₂H₅ | H |
| 19 | —C₂H₅ | H | —COC₁₆H₃₃ | B |
| 20 | -i-C₃H₇ | H | —COC₁₆H₃₃ | B |
| 21 | —C₁₀H₂₁ | H | —COC₁₁H₂₃ | A |
| 22 | —C₂H₅ | H | —CON(C₈H₁₇)₂ | A |
| 23 | -i-C₃H₇ | H | —CON(C₈H₁₇)₂ | A |
| 24 | —C₂H₅ | H | —CON(CH₃)(C₆H₄—NHSO₂C₁₆H₃₃) | A |
| 25 | —C₁₀H₂₁ | H | —CON(CH₃)₂ | H |
| 26 | —C₂H₅ | H | —COC₁₆H₃₃ (C=O) | A |

TABLE 2-continued $$R^1-\underset{R^3}{\underset{|}{C}}-\overset{O}{\overset{\|}{C}}-NH-\underset{Z}{\overset{OH}{\bigcirc}}-NH-\overset{O}{\overset{\|}{C}}-NH-\bigcirc-CN$$

| | R¹ | R² | R³ | Z* |
|---|---|---|---|---|
| 27 | -i-C₃H₇ | H | $-\underset{O}{\overset{\|}{C}}OC_{16}H_{33}$ | A |
| 28 | —C₄H₉ | H | $-\underset{O}{\overset{\|}{C}}OC_{16}H_{33}$ | H |
| 29 | —C₁₀H₂₁ | H | $-\overset{O}{\overset{\|}{P}}-(C_2H_5)_2$ | A |
| 30 | -i-C₃H₇ | H | $-\overset{O}{\overset{\|}{P}}-(OCH_3)(OC_{16}H_{33})$ | A |
| 31 | -i-C₁₀H₂₁ | H | $-\overset{O}{\overset{\|}{P}}-(OC_6H_5)_2$ | H |

*A = —O—⟨○⟩—OCH₃

B = —O—⟨○⟩—OC₈H₁₇

Coupler compounds of this invention can be prepared by reacting phenyl isocyanate or substituted phenyl isocyanates or alkyl acid halides or aryl acid halides with an appropriate aminophenol, such as 2-amino-5-nitrophenol or 2-amino-4-chloro-5-nitro phenol to form the 2-phenyl ureido or 2-carbonamido coupler moiety compounds. The nitro group can then be reduced to an amine and a separately prepared ballast moiety can be attached thereto by conventional procedures. Two-equivalent couplers can be prepared by known techniques, for example, by substitution of a 4-chloro group on the starting phenol. Details of such preparations are noted below relative to specific coupler compounds identified in Tables I and II.

SYNTHESIS Example 1

Coupler Compound No. 24 was prepared as follows:

A. Preparation of 2-(p-cyanophenylureido)-4-p-methoxyphenoxy-5-aminophenol (S-5)

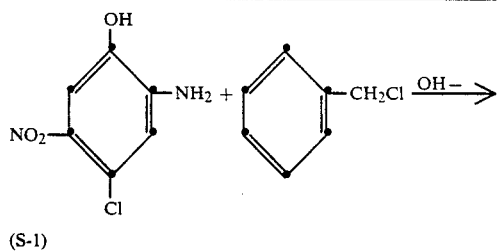

(S-1)

-continued

A. Preparation of 2-(p-cyanophenylureido)-4-p-methoxyphenoxy-5-aminophenol (S-5)

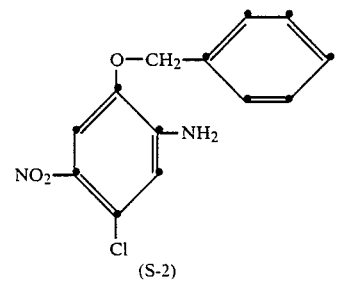

(S-2)

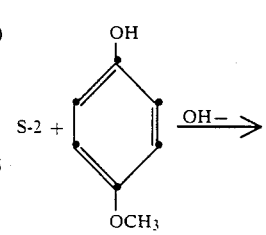

S-2 +     $\xrightarrow{OH^-}$

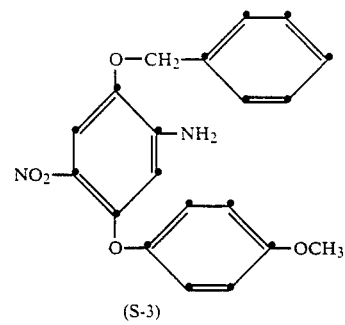

(S-3)

S-3 + OCN—⟨○⟩—CN ⟶

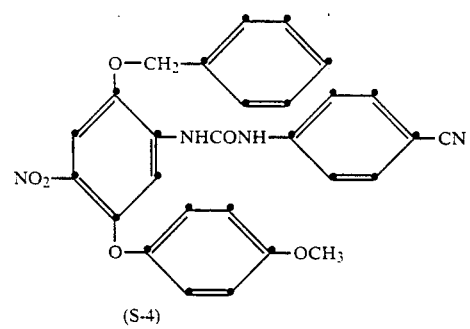

(S-4)

S-4 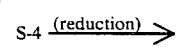

-continued
A. Preparation of 2-(p-cyanophenylureido)-4-p-methoxyphenoxy-5-aminophenol (S-5)

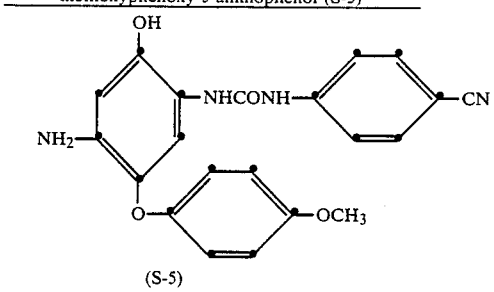

(S-5)

To a refluxing solution of 33.7 g (0.2 mol) 2-amino-4-chloro-5-nitrophenol (S-1) and 12.8 g (0.2 mol) potassium hydroxide in 300 ml acetone was added over a 3 hour period 25.3 g (0.2 mol)α-chloro-toluene. After an additional 6 hour reflux, the mixture was concentrated and added to cold potassium carbonate solution. The resulting precipitate was washed, dried, and recrystallized from xylene to yield 44.8 g yellow green solid S-2, m.p. 131°.

A solution of 9.4 g (0.076 mol) p-methoxyphenol and 3.4 g (0.076 mol) potassium hydroxide in 200 ml toluene was refluxed to remove the aqueous azeotrope, then cooled to 40°. Then 40 ml dimethyl sulfoxide and 12 g (0.043 mol) S-2 were added sequentially and the mixture was heated gradually and refluxed 1 hour. The cooled reaction mixture was washed with water and sodium carbonate solution, dried over magnesium sulfate and treated with carbon. The solid obtained by cooling and filtering was washed with toluene and hexane then dried to yield 11.5 g S-3.

This product was converted to S-4 by treatment with equimolar p-cyanophenylisocyanate according to a procedure analogous to that described in Example 1 of U.S. Pat. No. 4,333,999, the disclosure of which is incorporated herein by reference.

A suspension of 7.6 g (11.5 mmol) nitro compound S-4 in 150 ml ethylacetate was shaken overnight with 2 g 10% palladium on carbon catalyst and 1.0 ml acetic acid under 276 kPa (40 lb) hydrogen pressure to provide the aminophenol S-5.

B. Preparation of ballast acid chloride S-14:

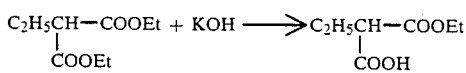

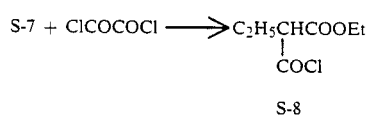

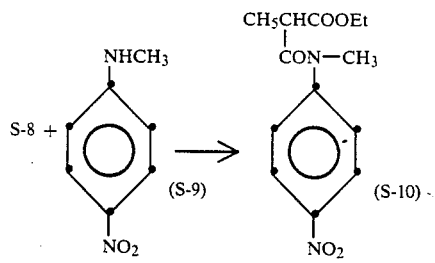

-continued
B. Preparation of ballast acid chloride S-14:

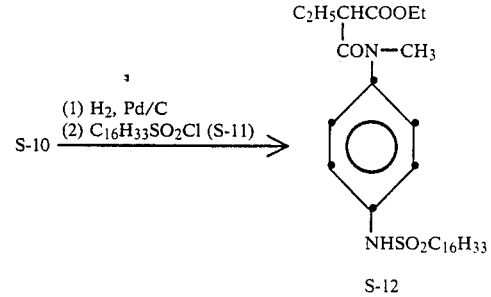

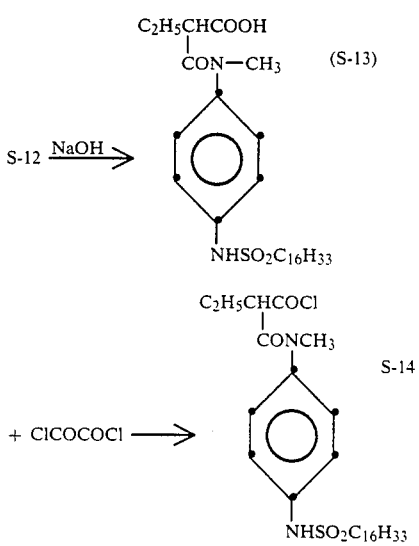

117.5 g (0.625 mole) diethyl ethylmalonate (S-6) dissolved in 400 ml ethanol is treated with 35 g (0.625 mole) potassium hydroxide dissolved in 400 ml ethanol: dropwise addition over 1.5 hr. After 20 hr stirring at ambient temperature, the ethanol solvent is removed under vacuum. The oily residue is taken up in water, washed with diethyl ether to remove impurities and then acidified to yield the pure oily product which is separated from the water by extraction with diethyl ether followed by concentration to give 80 g (S-7).

34.8 g (0.274 mol) oxalyl chloride an 10 drops Dimethylformamide were added to a stirred solution of 22 g (0.137 mol) S-7 acid in 250 ml dichloromethane. After 1.5 hour the mixture was concentrated to yield the acid chloride S-8 as a yellow oil.

24.4 g (0.237 mol) of S-8 acid chloride is added to a stirred solution of 20.9 g (0.137 mol) N-methyl-p-nitro analine (S-9) and 25 g (0.206 moles) N,N-dimethyl analine dissolved in 600 ml ethyl acetate. After stirring for 2 hours at ambient temperature, the reaction mixture was washed twice with 10% HCl, dried and concentrated to a yellow oil. Purification by chromatography yielded 30 g S-10 as a clear yellow oil.

28.4 g (0.097 mol) of S-10 was dissolved in 150 ml tetrahydrofuran and then was shaken under 276 kPa (40 lbs) hydrogen pressure with 2 ml acetic acid and 2 g 10% palladium on carbon to give an amine intermediate which was immediately treated with 34.7 g (0.107 mol) hexadecyl sulfonyl chloride (S-11) and 100 ml pyridine. After 4 hours stirring at ambient temperature, the reaction mixture was quenched in excess 10% HCl, followed by extraction with ethyl acetate and concentration to an orange oil. Purification by chromatography yielded 46 g of S-12 as a light orange oil.

To 46 g (0.0832 mol) of ester S-12 dissolved in a 2:1 mixture of tetrahydrofuran and methanol is add 25 g (0.625 mol) sodium hydroxide dissolved in water. After stirring at ambient temperature for 1.5 hours, the reaction mixture was quenched in excess 10% HCl, extracted with ethyl acetate, dried and concentrated to a solid which was purified by crystallization from acetonitrile to give 35 g S-13.

7.9 g (0.015 mol) S-13 acid in 150 ml dichloromethane was treated with 2.6 ml (0.030 mol) oxalyl chloride and 10 drops dimethylformamide, stirred for 1.5 hours, and concentrated to yield 8.2 g ballast acid chloride S-14 as a yellow oil.

C. Synthesis of Coupler Compound No. 24

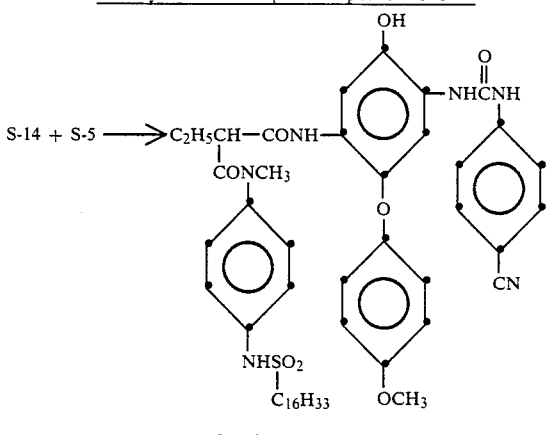

Coupler No. 24

To a stirred solution of 5.3 g (0.0136 mol) of the S-5 amine and 3.6 g (0.030 mol) N-N-dimethylanaline in 300 ml ethyl acetate is added 8.2 g (0.0150 mol) of ballast acid chloride (S-14). After stirring for 0.5 hr, the reaction mixture is washed three times with 10% HCl, dried and concentrated to a glassy solid. Purification by chromatography and crystallization from methanol yielded 5.2 g of Coupler No. 24 as a white solid with a melting point of 131-2 degree C. Mass Spec., elemental analysis and NMR confirm product structure.

SYNTHESIS EXAMPLE 2

Coupler Compound No. 26 was prepared as follows:

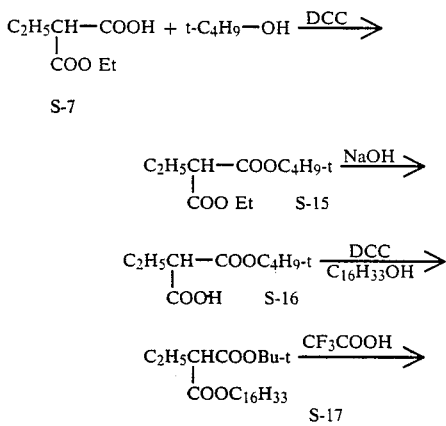

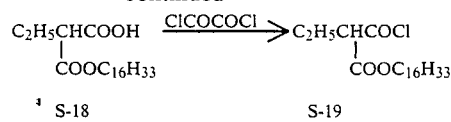

S-19 + S-5 ⟶

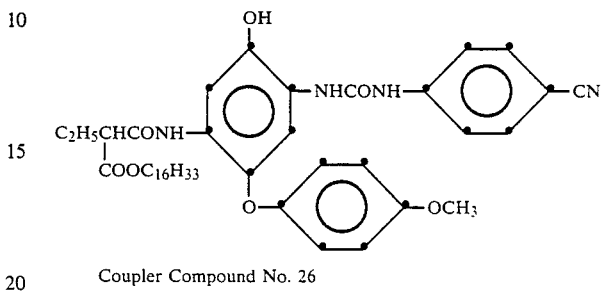

Coupler Compound No. 26

A dichloromethane solution of 42 g (0.204 mol) dicyclohexylcarbodiimide (DCC) is added dropwise (0.5 hours) to a well stirred solution of 30 g (0.186 mol) S-7 acid (from Synthesis Example 1), 27.6 g (0.372 mol) t-butyl alcohol and 0.2 g 4 dimethylaminopyridine (catalyst) in 500 ml dichloromethane. After stirring at ambient temperature for 20 hours, the dicyclohexylurea by-product is filtered off and the filtrate is concentrated to an oil. Purification by chromatography yielded 26 g of the mixed diester S-15 as an oil.

A solution of 14.4 g (0.360 mol) sodium hydroxide in 60 ml water is chilled to <10 degrees C. and is then added to a chilled (<0° C.) and well stirred solution of 24 g (0.111 mol) of diester S-15 dissolved in 120 ml tetrahydrofuran and 60 ml methanol. After stirring at 0 degree C. for 1 hour, the reaction mixture is poured into excess 10% HCl which had been chilled to 0 degree C., extracted with ethyl cetate, dried and concentrated to 22 g of mono-acid S-16 as a clear colorless oil.

A solution of 23 g (0.11 mol) dicyclohexylcarbodiimide (DCC) in 50 ml dichloromethane is added dropwise (0.5 hour) to a well stirred solution of 19 g (0.10 mol) of S-16 acid, 30 g (0.125 mol) hexadecyl alcohol and 0.2 g 4-dimethylaminopyridine (catalyst) dissolved in 300 ml dichloromethane. After stirring at ambient temperature for 3 hours, the dicyclohexyl urea by-product is filtered off and the filtrate is concentrated to an oil. Purification by chromatography yielded 32 g of mixed diester S-17 as a clear light yellow oil.

A solution of 15 g (0.0363 mol) diester S-17 in 18 ml trifluoroacetic acid was stirred at ambient temperature for 0.5 hour, and was then poured onto ice and extracted with ethyl acetate. The extract was washed several times with water, dried and concentrated to an oil. Purification by chromatography yielded 10.0g of acid S-18 as a white solid.

3.3 ml (0.0375 mol) oxalyl chloride and 10 drops of dimethylformamide are added to a stirred solution of 8.8 g (0.025 mol) S-18 acid in 150 ml dichloromethane. After 1 hour stirring at ambient temperature, the mixture is concentrated to yield 9.3 g of the acid chloride S-19 as a yellow oil. Synthesis of Coupler No. 26:

Under a blanket of nitrogen, 9.3 g (0.025 mol) of ballast acid chloride S-19 is added to a stirred solution of 8.3 g (0.0214 mol) of the parent coupler amine S-5 (see Synthesis Example 1) and 5.2 g (0.043 mol) N,N-dimethylanaline in 300 ml ethyl acetate. After stirring at ambient temperature for 0.5 hour, the reaction mixture was washed 3 times with 10% HCl, dried and concentrated to a dark glassy solid. Purification by chromatography and crystallization from acetonitrile yielded 8.2 g of Coupler Compound No. 26 having a melting point of 147-8 degree C. Mass Spec, NMR and elemental analysis confirm product structure.

SYNTHESIS EXAMPLE 3

Coupler Compound No.16 was prepared as follows:

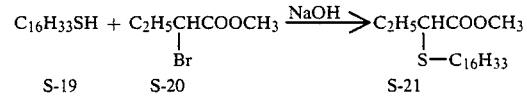

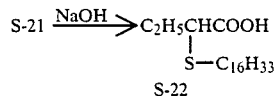

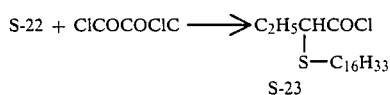

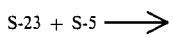

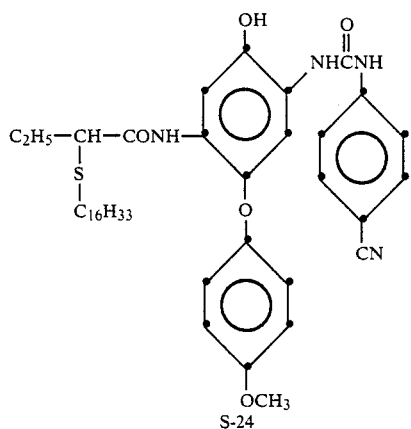

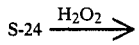

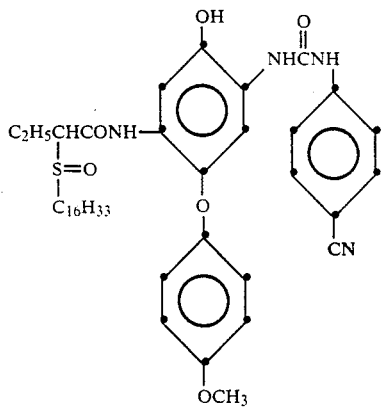

Coupler Compound No. 16

To a well stirred solution of 258.4 g (1.0 mol) n-hexadecyl mercaptan (S-19) and 217 g (1.2 mol) methyl alpha-bromobutyrate (S-20) in 500 ml ethanol was added, under nitrogen, a solution of 44 g (1.1 mol) sodium hydroxide in 300 ml water. After 1 hour a solution of 80 g (2.0 mol) sodium hydroxide in 1 liter tetrahydrofuran and 750 ml methanol was added and stirring continued 2 hours to hydrolyze the S-21 ester to the S-22 acid sodium salt. This salt, which precipitated on concentration of the reaction mixture, was suspended in 4.5 liters dilute hydrochloric acid and stirred 1 hour to yield 350 g moist white solid S-22 acid.

3.6 g (0.029 mol) oxalyl chloride and 10 drops dimethylformamide were added to a stirred solution of 5.0 g (0.0145 mol) S-22 ballast acid in 150 ml dichloromethane. After 1.5 hour stirring at ambient temperature, the mixture was concentrated to yield the acid chloride S-23 as a gummy white residue.

5.3 g (0.0145 mol) of the ballast acid chloride (S-23) was added under a blanket of nitrogen to a stirred solution of 5.6 g (0.0145 mol) of the parent coupler amine S-5 (see Synthesis Example 1) and 3.5 g (0.029 mol) N,N-dimethylanaline dissolved in 300 ml ethyl acetate. After stirring for 0.5 hour at ambient temperature, the reaction mixture was washed 3 times with 10% HCL and extracted with ethyl acetate. The extract is dried and concentrated to a dark glass. Purification by chromatography and crystallization from acetonitrile yielded 6.7 g of coupler S-24 as a tan solid.

SYNTHESIS OF COUPLER COMPOUND NO. 16

1.9 ml (0.189 mol) 30% aqueous hydrogen peroxide was added dropwise over 0.5 hour to a stirred solution of of 9.1 g (0.0127 mol) of coupler S-24 dissolved in a mixture of 100 ml acetic acid and 25 ml tetrahydrofuran. After stirring for 2 hours at ambient temperature, the reaction mixture was poured into 800 ml cold water and extracted with ethyl acetate. The extract was dried and concentrated to a dark yellow oil. Purification by chromatography and crystallization from acetonitrile yielded 3.3 g of coupler Compound No. 16 as a tan solid with a melting point of 156-8 degree C. Mass Spec, IR and elemental analysis confirm product structure.

SYNTHESIS EXAMPLE 4

Coupler No. 21 was prepared according to the following scheme:

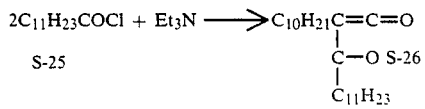

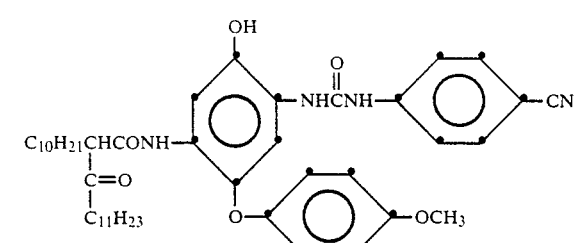

Coupler Compound No. 21

20 8 g (0.20 mol) triethylamine dissolved in 70 ml anhydrous diethyl ether is added dropwise over minutes to a stirred and ice water bath chilled solution of 43.6 g (0.20 mol) lauryl chloride (S-25) dissolved in 350 ml anhydrous ethyl ether. Removed cooling bath and allowed to stand for 20 hours at ambient temperature. Filtered off the triethylamine hydrochloride salt byproduct and concentrated the ether filtrate to a yellow oil. Crystallized from cold acetone to yield 10 g of S-26 as a cream colored solid.

10.7 g (0.030 mol) of the S-26 ketene is added under nitrogen to a stirred solution of 7.8 g (0.02 ml) parent coupler amine S-5 (see Synthesis Example 1) in 300 ml dioxane. The reaction mixture is stirred under nitrogen while being heated with a steam bath for 24 hours. Cooled to room temperature and poured reaction mixture into cold water and extracted with ethyl acetate. Dried the extract and concentrated to a dark gum. Purification by chromatography and crystallization from acetonitrile yielded 5.5 g of coupler Compound No. 21 as a white solid with a melting point of 138–9 degree C. Mass Spec, IR and elemental analysis confirmed product structure.

The cyan dye forming couplers described herein can be used in the ways and for the purposes that cyan dye-forming couplers are used in the photographic art. Typically, the couplers are incorporated in silver halide emulsions and the emulsions coated on a support to form a photographic element. Alternatively, the couplers can be incorporated in photographic elements adjacent the silver halide emulsion where, during development, the coupler will be in reactive association with development products such as oxidized color developing agent.

The cyan dye-forming couplers described herein can be combined with development inhibitor releasing compounds having the structure:

where CAR is a carrier moiety, TIME is a timing and INH is a development inhibitor moiety. Such combination enhances the sharpness of cyan images obtained from the described couplers.

The INH development inhibitor moiety is more fully described in co pending U.S. patent application Ser. No. 213,415 filed June 30, 1988 the disclosure of which is incorporated herein by reference.

As used herein, the term "associated therewith" signifies that the coupler is in the silver halide emulsion layer or in an adjacent location where, during processing, it is capable of reacting with silver halide development products.

The photographic elements can be either single color or multicolor elements. In a multicolor element, the cyan dye-forming coupler of this invention is usually associated with a red-sensitive emulsion, although it could be associated with an unsensitized emulsion or an emulsion sensitized to a different region of the spectrum. Multicolor elements contain dye image-forming units sensitive to each of the three primary regions of the spectrum. Each unit can be comprised of a single emulsion layer or of multiple emulsion layers sensitive to a given region of the spectrum. The layers of the element, including the layers of the image-forming units, can be arranged in various orders as known in the art.

A typical multicolor photographic element comprises a support bearing a cyan dye image-forming unit comprising of at least one red-sensitive silver halide emulsion layer having associated therewith at least one cyan dye-forming coupler, at least one of the cyan dye-forming couplers being a coupler of this invention, a magenta dye image-forming unit comprising at least one green-sensitive silver halide emulsion layer having associated therewith at least one magenta dye-forming coupler and a yellow dye image-forming unit comprising at least one blue sensitive silver halide emulsion layer having associated therewith at least one yellow dye-forming coupler. The element can contain additional layers, such as filter layers, interlayers, overcoat layers, subbing layers, and the like.

In the following discussion of suitable materials for use in the elements of this invention, reference will be made to Research Disclosure, December 1978, Item 17643, published by Kenneth Mason Publications, Ltd., The Old Harbourmaster's, 8 North Street, Emsworth, Hampshire P0107DD, ENGLAND, the disclosures of which are incorporated herein by reference. This publication will be identified hereafter by the term "Research Disclosure."

The silver halide emulsions employed in the elements of this invention can be either negative-working or positive-working. Suitable emulsions and their preparation are described in Research Disclosure Section I and II and the publications cited therein. Tabular photographic silver halide grains are also useful. Such tabular grain silver halide is described in, for example, U.S. Pat. No. 4,434.226 and in *Research Disclosure*. January 1983, Item No. 22534. Suitable vehicles for the emulsion layers and other layers of elements of this invention are described in Research Disclosure Item 17643, Section IX and the publications cited therein.

In addition to the couplers described herein the elements of this invention can include additional couplers as described in Research Disclosure Section VII, paragraphs D, E, F and G and the publications cited therein. These additional couplers can be incorporated as described in Research Disclosure Section VII, paragraph C and the publications cited therein.

The photographic elements of this invention can contain brighteners (Research Disclosure Section V), antifoggants and stabilizers (Research Disclosure Section VI), antistain agents and image dye stabilizers (Research Disclosure Section VII, Paragraphs I and J), light absorbing and scattering materials (Research Disclosure Section VIII), hardeners (Research Disclosure Section XI), Plasticizers and lubricants (Research Disclosure Section XII), antistatic agents (Research Disclosure Section XIII), matting agents (Research Disclosure Section XVI) and development modifiers (Research Disclosure Section XXI).

The photographic elements can be coated on a variety of supports as described in Research Disclosure Section XVII and the references described therein.

Photographic elements can be exposed to actinic radiation, typically in the visible region of the spectrum, to form a latent image as described in Research Disclosure Section XVIII and then processed to form a visible dye image as described in Research Disclosure Section XIX. Processing to form a visible dye image includes the step of contacting the element with a color developing agent to reduce developable silver halide and oxidize the color developing agent. Oxidized color developing agent in turn reacts with the coupler to yield a dye.

Preferred color developing agents ae p-phenylene diamines. Especially preferred are 4-amino-3-methyl-N,N-diethylaniline hydrochloride, 4-amino-3-methyl-N-ethyl-N-β-(methanesulfonamido)-ethylaniline sulfate hydrate, 4-amino-3-methyl-N-ethyl-N-β-hydroxyethylaniline sulfate, 4-amino-3-β-(methanesulfonamido)ethyl-N,N-diethylaniline hydrochloride and 4-amino-N-ethyl-N-(2-methoxyethyl)-m-toluidine di-p-toluene sulfonic acid.

With negative working silver halide this processing step leads to a negative image. To obtain a positive (or reversal) image, this step can be preceded by development with a non chromogenic developing agent to develop exposed silver halide, but not form dye, and then uniform fogging of the element to render unexposed silver halide developable. Alternatively, a direct positive emulsion can be employed to obtain a positive image.

Development is followed by the conventional steps of bleaching, fixing, or bleach-fixing to remove silver and silver halide, washing and drying.

In the following examples, a measure of each coupler's coupling effectiveness is represented by G which is the ratio of its photographic dye image gamma (the slope of the sensitometric curve) to that of Control Coupler A. Such normalization of the data compensates for coating and processing variations by relating the performance of each test coupler as described herein to that of a control coupler coated and processed at the same time and in the same manner. In these comparisons 2-equivalent couplers were coated at one half the silver level of 4-equivalent couplers.

Processing and testing procedures were kept constant. Particularly useful couplers provided dye images with G>1.00, and Dmax/Dmax, control values of >1.00.

EXAMPLE 1

Photographic elements were prepared by coating a cellulose acetate film support with a light-sensitive layer comprising a silver bromoiodide (6.5 mol % I) emulsion at 0.91 Ag/m²; gelatin at 3.78 g/m² containing a cyan phenolic coupler identified by number as shown above in Tables 1 or 2. Each coupler was dispersed with one half its weight of di-n-butyl phthalate and coated at $1.62 \times 10^{-3}$ mols/m². The photosensitive layer was overcoated with a layer containing gelatin at 1.08 g/m² and the hardener compound bis vinylsulfonylmethyl ether at 1.75 weight percent based on total gelatin.

Samples of each element were imagewise exposed through a graduated-density test object and processed at 40° C. employing the following color developing solution, then stopped, bleached with a ferric EDTA 9 (ethylenediaminetetraacetic acid) solution, fixed, and washed to produce stepped cyan dye images.

| | | |
|---|---|---|
| K₂SO₃ | 2.0 g | |
| K₂CO₃ (anhydrous) | 30.0 g | |
| KBr | 1.25 g | |
| KI | 0.6 mg | |
| 4-Amino-3-methyl-N-ethyl N-β-hydroxyethylaniline sulfate | 3.55 g | |
| Water to 1.0 liter | pH 10.0 | |

Results are noted below in Table III:

TABLE III

| Compound | G | Dmax/Dmax. Control |
|---|---|---|
| Control Coupler A | 1.00 | 1.00 |
| 21 | 1.34 | 1.90 |
| 16 | 1.26 | 1.75 |
| 24 | 1.02 | 1.14 |
| 26 | 2.18 | 1.72 |

Control Coupler A:

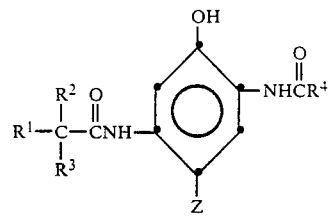

which falls within the description of U.S. Pat. No. 4,333,999.

This invention has been described in detail with particular reference to preferred embodiments thereof, but it will be understood that variations and modifications can be effected within the spirit and scope of the invention.

What is claimed is:

1. A photographic recording material comprising a support and a photosensitive silver halide emulsion which has associated therewith a cyan dye-forming coupler compound having the structural formula:

wherein:
$R^1$ is an unsubstituted or a substituted, straight or branched chain alkyl group having from 1 to about 20 carbon atoms, an unsubstituted or a substituted cycloalkyl group having from 3 to about 8 carbon atoms in the ring or an unsubstituted or a substituted aryl group;

$R^2$ is hydrogen or as defined for $R^1$;

$R^3$ is a ballast group comprising one of the following:
(a) a sulfoxide containing group having the formula $R^5SO-$;
(b) an amide containing group having the formula $R^6R^7NCO-$;
(c) an ester containing group having the formula $R^5OCO-$;
(d) a ketone containing group having the formula $R^5CO-$; or
(e) a phosphine oxide containing group having the formula

R[4] represents an unsubstituted linear or branched aliphatic group or a linear or branched aliphatic group substituted with one or more substituents selected from halogen, alkoxy. alkylthio, arylthio, alkylsulfonyl, arylsulfonyl, sulfonamido, acylamino, alkyloxycarbonyl, aryloxycarbonyl, carbamoyl, alkylcarbonylocy, arylcarbonyloxy, carboxyl and hydroxyl; or R[4] represents

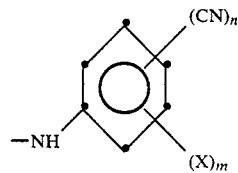

where X is —COOR[10], —COR[10], —SO$_2$OR[10], —SO$_2$R[10],

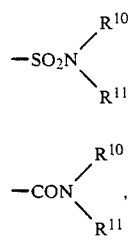

—NO$_2$, —CF$_3$, hydrogen, halogen, hydroxy or a monovalent orgainc group;

R[5] is alkyl or aryl which may be substituted;

R[6] and R[7], which may be the same or different, represent hydrogen or are as defined for R[5];

R[8] and R[9], which may be the same or different, represent alkyl, alkoxy, aryl or aryloxy which may be substituted;

R[10] is an alkyl group having up to 16 carbon atoms or an aryl group having from 6 to 12 carbon atoms;

R[11] is hydrogen, or as defined for R[10];

n is 0, 1 or 2;

m is 3 to 5; and

Z is hydrogen or a coupling off group;

with the proviso that at least one of R[1], R[2], R[3] or Z is of such size and configuration as to render the coupler compound substantially nondiffusible in the layer of a photographic recording material in which it is coated.

2. The photographic material of claim 1 wherein R[2] is hydrogen or alkyl having from 1 to about 4 carbon atoms.

3. The photographic material of claim 1 wherein R[1] is alkyl having from 1 to about 14 carbon atoms and R[2] is hydrogen.

4. The photographic material of claim 1 wherein R[4] represents

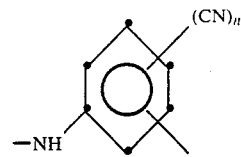

ps where X is —COOR[10], —COR[10], —SO$_2$OR[10], —SO$_2$R[10],

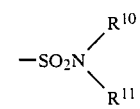

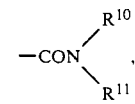

—NO$_2$, —CF$_3$, hydrogen, halogen hydroxy or a monovalent organic group.

5. The photographic material of claim 4 wherein X is hydrogen, m is 4 and n is 1.

6. The photographic material of claim 1 wherein R[5] is alkyl having 1 to about 24 carbon atoms.

7. The photographic material of claim 1 wherein Z is hydrogen or

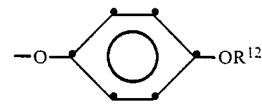

where R[12] is an alkyl group having from 1 to about 10 carbon atoms.

8. The photographic material of claim 1 wherein the cyan dye-forming coupler compound has the structural formula:

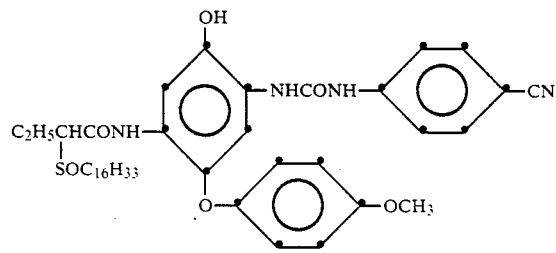

9. The photographic material of claim 1 wherein the cyan dye-forming coupler compound has the structural formula:

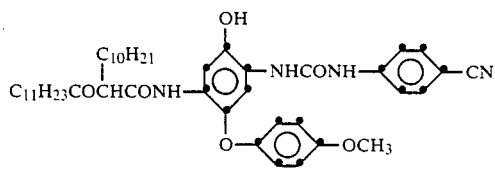

10. The photographic material of claim 1 wherein the cyan dye-forming coupler compound has the structural formula:

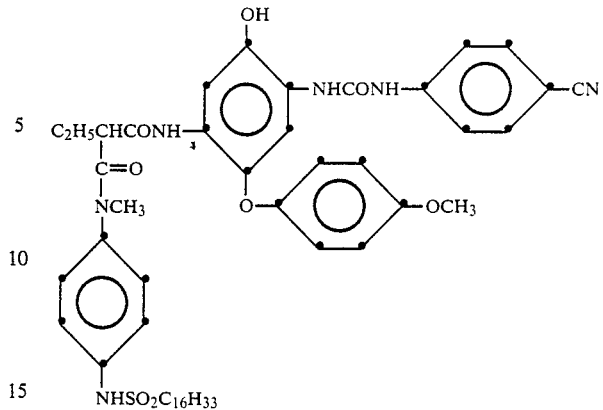
11. The photographic material of claim 1 wherein the cyan dye-forming coupler compound has the structural formula:
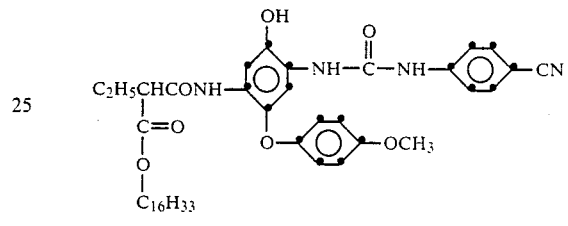
* * * * *